(12) United States Patent
Tanaka

(10) Patent No.: US 12,710,492 B2
(45) Date of Patent: Aug. 18, 2026

(54) MAGNETIC RESONANCE IMAGING APPARATUS

(71) Applicant: Canon Kabushiki Kaisha, Tokyo (JP)

(72) Inventor: Yu Tanaka, Ota-ku (JP)

(73) Assignee: Canon Kabushiki Kaisha, Tokyo (JP)

( * ) Notice: Subject to any disclaimer, the term of this patent is extended or adjusted under 35 U.S.C. 154(b) by 119 days.

(21) Appl. No.: 18/641,508

(22) Filed: Apr. 22, 2024

(65) Prior Publication Data

US 2024/0377489 A1 Nov. 14, 2024

(30) Foreign Application Priority Data

May 12, 2023 (JP) ................................ 2023-079627

(51) Int. Cl.

*G01V 3/00* (2006.01)
*A61B 5/055* (2006.01)
*G01R 33/36* (2006.01)

(52) U.S. Cl.

CPC .......... *G01R 33/3607* (2013.01); *A61B 5/055* (2013.01)

(58) Field of Classification Search

CPC ............................ G01R 33/3607; A61B 5/055
USPC .......................................................... 324/307
See application file for complete search history.

(56) References Cited

U.S. PATENT DOCUMENTS

2016/0125951 A1* 5/2016 Sun ...................... G11C 29/028 365/185.24
2017/0082706 A1* 3/2017 Soejima ................. G01R 33/34

FOREIGN PATENT DOCUMENTS

CN 101453222 A * 6/2009
CN 106797482 A * 5/2017 ............ H04N 19/70
JP 2003114618 A * 4/2003
JP 2014-57872 A 4/2014
KR 101907647 B1 * 10/2018 ............... H03B 5/12
WO WO-03055161 A2 * 7/2003 ............ H04L 27/02

* cited by examiner

*Primary Examiner* — Walter L Lindsay, Jr.
*Assistant Examiner* — Frederick Wenderoth
(74) *Attorney, Agent, or Firm* — Oblon, McClelland, Maier & Neustadt, L.L.P.

(57) ABSTRACT

A magnetic resonance imaging apparatus according to an embodiment includes a main apparatus and a coil apparatus that is separate from the main apparatus. The main apparatus transmits a wireless signal acquired by frequency-modulating a binary signal based on a first clock signal generated from a first system clock. The coil apparatus generates a second clock signal by dividing the received wireless signal, and generates a second system clock from the generated second clock signal. Frequencies of the second system clock and the first system clock are the same.

11 Claims, 8 Drawing Sheets

101
GRADIENT MAGNETIC FIELD POWER SUPPLY
105
RF PULSE/ GRADIENT MAGNETIC FIELD CONTROL UNIT
110
RF PULSE GENERATION UNIT
109
103
104
108
WIRELESS UNIT
112
DATA ANALYSIS UNIT
113
102
118
106
106a
108
104
103
CLOCK GENERATION UNIT
111
COUCH CONTROL UNIT
107
IMAGING CONTROL UNIT
117
STORAGE UNIT
114
DISPLAY UNIT
115
INPUT UNIT
116

FIG.2

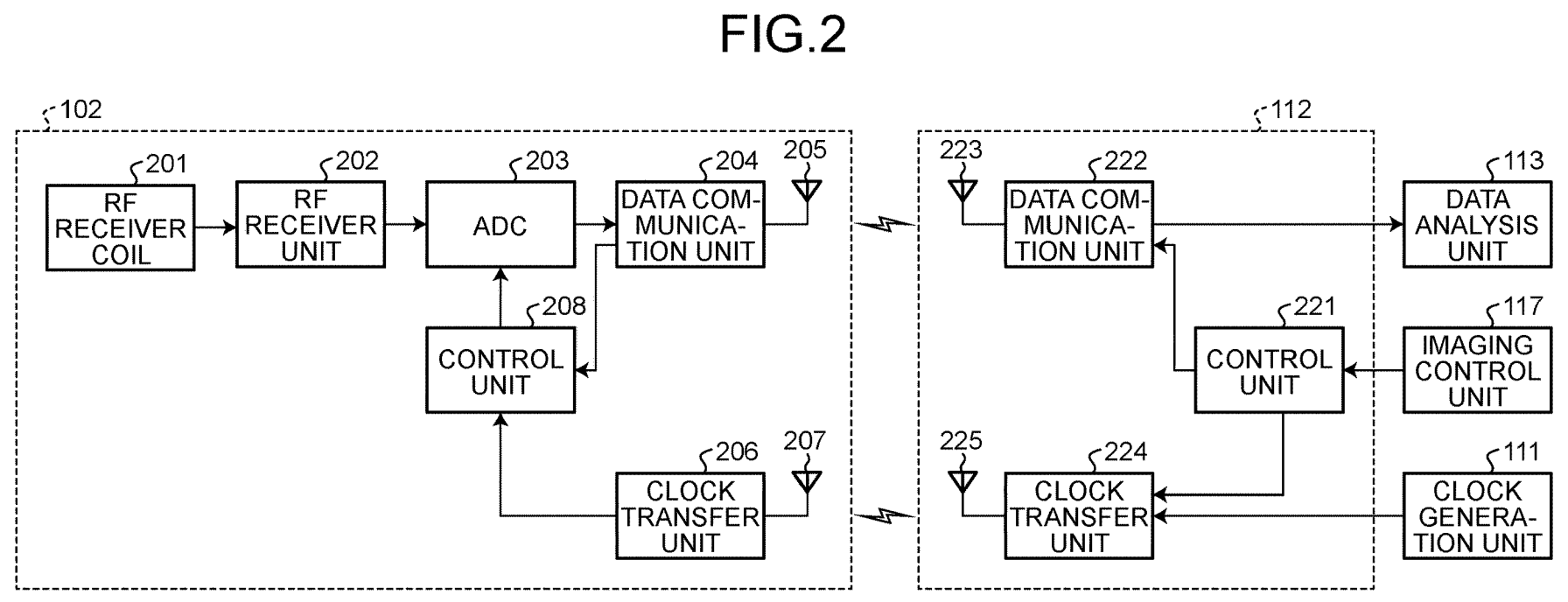

102
201 RF RECEIVER COIL
202 RF RECEIVER UNIT
203 ADC
204 DATA COMMUNICATION UNIT
205
206 CLOCK TRANSFER UNIT
207
208 CONTROL UNIT 112
221 CONTROL UNIT
222 DATA COMMUNICATION UNIT
223
224 CLOCK TRANSFER UNIT
225

113 DATA ANALYSIS UNIT
117 IMAGING CONTROL UNIT
111 CLOCK GENERATION UNIT

221
CONTROL UNIT
111
CLOCK GENERATION UNIT
224
301
CODE SIGNAL GENERATION UNIT
302
CLOCK TRANSMITTER UNIT
225
Sdl
207
303
CLOCK RECEIVER UNIT
206
208
CONTROL UNIT

221
CONTROL UNIT
111
CLOCK GENERATION UNIT
301
401
PN9 GENERATION UNIT
402
ADJUSTMENT DATA ADDITION UNIT
403
TRANSMISSION BUFFER
404
8B10B CONVERSION UNIT
302
CLOCK TRANSMITTER UNIT

FIRST CLOCK SIGNAL
ENCODING
CODE SIGNAL
FREQUENCY MODULATION
WIRELESS CLOCK SIGNAL
f1
DIVIDING
SECOND CLOCK SIGNAL
PLL
SYSTEM CLOCK

CODE SIGNAL
1
0
FREQUENCY MODULATION
+f2
-f2
f1
PLL OUTPUT
+f2
-f2
f1

TR
TE
TE
RF PULSE
Gs
Ge
Gr
MR SIGNAL
WIRELESS CLOCK SIGNAL
701
702
703
704
705
706
707
708
709
t

901 SOF

902 PAYLOAD

903 CORREC-TION BIT

MAGNETIC RESONANCE IMAGING APPARATUS

CROSS-REFERENCE TO RELATED APPLICATIONS

This application is based upon and claims the benefit of priority from Japanese Patent Application No. 2023-079627, filed on May 12, 2023; the entire contents of which are incorporated herein by reference.

FIELD

Embodiments described herein relate generally to a magnetic resonance imaging apparatus.

BACKGROUND

A magnetic resonance imaging (MRI) apparatus is an imaging apparatus that excites the nuclear spins of a subject placed in a static magnetic field with radio frequency (RF) signals at Larmor frequency, and generate images by reconstring the images from magnetic resonance (MR) signals generated from the subject.

In an MRI apparatus, RF pulses are transmitted from a main unit toward the subject. The MR signals emitted from the subject in response to the transmission are received by a coil unit. The coil unit receives the MR signals emitted from the subject at a position close to the subject. As for the coil unit, there are various types such as for the head, chest, spine, and lower limbs, depending on the imaging areas of the subject.

Conventionally, wired coil units that transfer received MR signals to the main unit by wire are often used. In contrast, a wireless coil unit has been proposed, which converts received MR signals from analog signals to digital signals using an analog to digital converter (ADC) and wirelessly transfers the digitized MR signals to the main unit.

When using a wired coil unit, MR signals sent as analog signals from the coil unit to the main unit are analog-to-digital converted on the main unit side using a sampling clock generated from a system clock on the main unit side.

On the other hand, when using a wireless coil unit, a sampling clock for analog-to-digital converting the MR signals is required on the coil unit side, and a system clock for generating the sampling clock is also required on the coil unit side.

Note here that the system clock on the coil unit side and the system clock on the main unit side need be synchronized with each other. Thus, if there is a phase shift between those clocks, accuracy of the image to be reconstructed may be lowered.

For example, as a conventional technology, a method of synchronizing clocks using wireless communication has also been proposed. However, this method may cause a phase shift between the system clock on the coil unit side and the system clock on the main unit side due to the effects of fading caused on the wireless propagation path. In addition, since the wireless coil unit is battery-driven, it is desired to have low power consumption.

BRIEF DESCRIPTION OF THE DRAWINGS

FIG. 2 is a block diagram illustrating functional configurations of a coil unit and a wireless unit;

DETAILED DESCRIPTION

An MRI apparatus according to an embodiment includes a main apparatus and a coil apparatus that is separate from the main apparatus. The main apparatus transmits a wireless signal acquired by frequency-modulating a binary signal based on a first clock signal generated from a first system clock. The coil apparatus generates a second clock signal by dividing the received wireless signal, and generates a second system clock from the generated second clock signal. Frequencies of the second system clock and the first system clock are the same.

Embodiment

Hereinafter, an MRI apparatus according to the present embodiment will be described with reference to the accompanying drawings.

Figure 1:
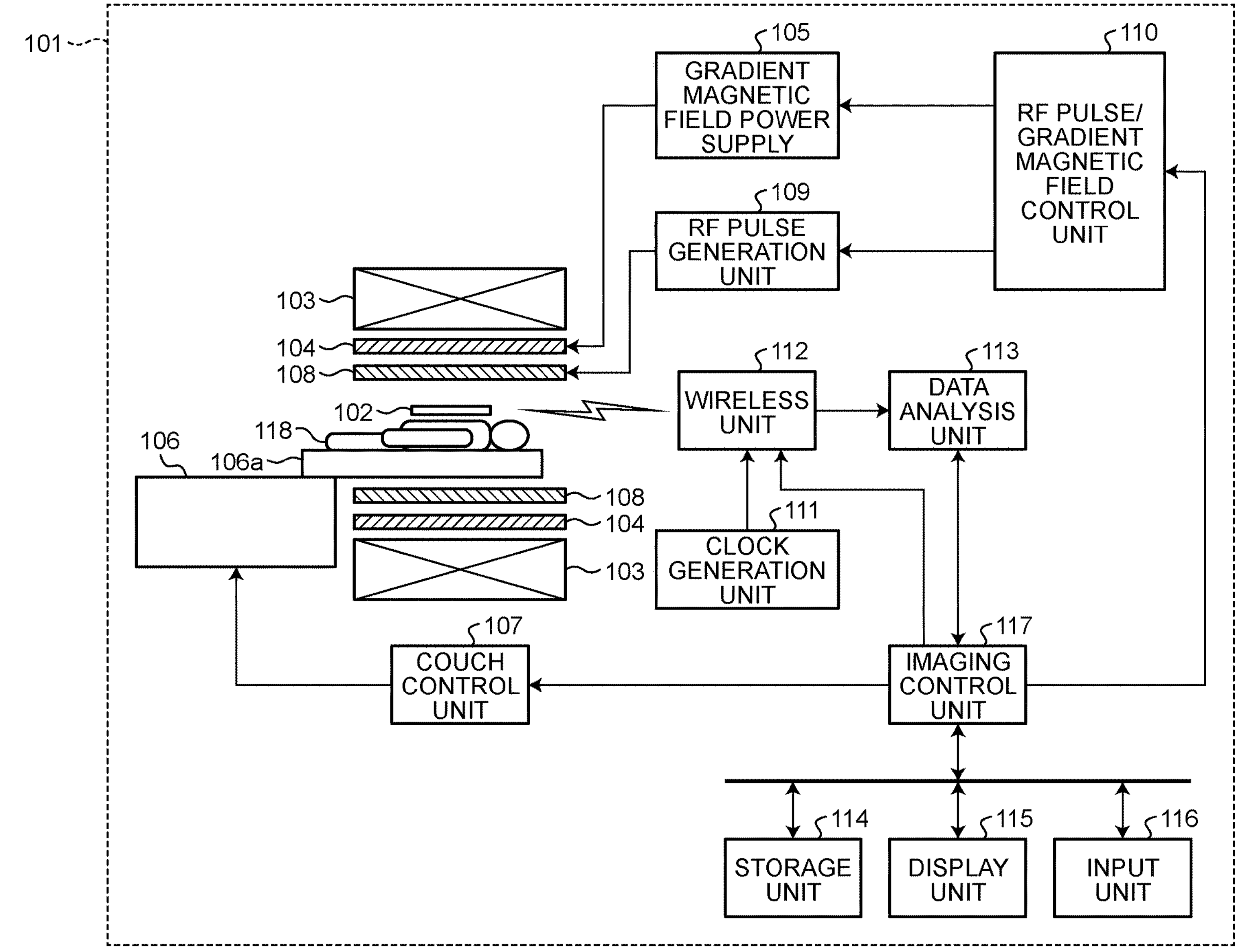
FIG. 1 is a diagram illustrating a configuration example of an MRI apparatus.

FIG. 1 is a diagram illustrating a configuration example of the MRI apparatus.

The MRI apparatus includes a main unit 101 and a coil unit 102. The main unit 101 includes a static magnetic field magnet 103, a gradient coil 104, a gradient magnetic field power supply 105, a couch 106, a couch control unit 107, a transmitter coil 108, an RF pulse generation unit 109, an RF pulse/gradient magnetic field control unit 110, a clock generation unit 111, a wireless unit 112, a data analysis unit 113, a storage unit 114, a display unit 115, an input unit 116, and an imaging control unit 117. Note that the main unit 101 may also be divided into a gantry and a processing unit. In this case, for example, the static magnetic field magnet 103, the gradient coil 104, the gradient magnetic field power supply 105, the couch 106, the couch control unit 107, the transmitter coil 108, the RF pulse generation unit 109, the RF pulse/gradient magnetic field control unit 110, and the wireless unit 112 are provided in the gantry, and the clock generation unit 111, the data analysis unit 113, the storage unit 114, the display unit 115, the input unit 116, and the imaging control unit 117 are provided in the processing unit. Note here that the main unit 101 is an example of the main apparatus. The coil unit 102 is also an example of the coil apparatus.

The static magnetic field magnet 103 has a hollow cylindrical shape, and generates a uniform static magnetic field in the inside space. For example, a resistive magnet, a superconducting magnet, or the like is used as this static magnetic field magnet 103.

The gradient coil 104 has a hollow cylindrical shape, and it is disposed on the inner side of the static magnetic field magnet 103. The gradient coil 104 is a combination of three kinds of coils corresponding to the X, Y, and Z axes orthogonal to each other. By receiving current supply at the three kinds of coils individually from the gradient magnetic field power supply 105, the gradient coil 104 generates gradient magnetic fields whose magnetic field strength is inclined along each of the X, Y, and Z axes. Note that the Z-axis direction is the same direction as the static magnetic field direction, for example. The gradient magnetic fields of the X, Y, and Z axes correspond, for example, to a slice selection gradient magnetic field Gs, a phase encoding gradient magnetic field Ge, and a readout gradient magnetic field Gr, respectively. The slice selection gradient magnetic field Gs is used to determine an imaging cross section as desired. The phase encoding gradient magnetic field Ge is used to change the phase of the MR signal in accordance with spatial location. The readout gradient magnetic field Gr is used to change the frequency of the MR signal in accordance with a spatial location.

The couch 106 moves a couchtop 106*a* in the longitudinal direction (left-and-right direction in FIG. 1) and the up-and-down direction under the control of the couch control unit 107. Normally, the couch 106 is installed such that the longitudinal direction is parallel to the central axis of the static magnetic field magnet 103. A subject 118 is placed on the couchtop 106*a*. The couch 106 inserts the subject 118 into the space (imaging space) inside the gradient coil 104 by moving the couchtop 106a.

The transmitter coil 108 is configured by housing a single or a plurality of coils in a cylindrical case. The transmitter coil 108 is disposed on the inner side of the gradient coil 104. The transmitter coil 108 receives supply of RF pulse signals from the RF pulse generation unit 109 and emits RF pulses.

The RF pulse generation unit 109 generates RF pulse signals.

The RF pulse/gradient magnetic field control unit 110 controls the gradient magnetic field power supply 105 and the RF pulse generation unit 109 according to pulse sequence information input from the imaging control unit 117. Note here that the pulse sequence information is information that specifies application timing of each of the gradient magnetic fields and the RF pulses, and the like.

The coil unit 102 is placed on the couchtop 106*a*, built into the couchtop 106*a*, or attached to the subject 118. Then, during imaging, the coil unit 102 is inserted into the imaging space together with the subject 118, and receives magnetic resonance echo emitted from the subject 118 to acquire electrical echo signals. The coil unit 102 transmits, to the wireless unit 112, echo data acquired by digitalizing the echo signals. Furthermore, the coil unit 102 receives wireless clock signals from the wireless unit 112 to synchronize the system clocks with each other.

The clock generation unit 111 generates a first clock signal from a first system clock at a prescribed frequency. The first clock signal is given to the wireless unit 112, and it is also used as the system clock that serves as the reference for the operation timing of the entire MRI apparatus. Note here that the clock generation unit 111 is an example of a clock signal generation unit.

The data analysis unit 113 analyzes the echo data, and reconstructs an image regarding the subject 118.

The storage unit 114 stores therein various kinds of data such as image data representing images reconstructed by the data analysis unit 113.

The display unit 115 displays various kinds of information such as images reconstructed by the data analysis unit 113 and various operation screens for allowing users to operate the MRI apparatus, under the control of the imaging control unit 117. As the display unit 115, it is possible to use a display device such as a liquid crystal display.

The input unit 116 receives various kinds of commands and information input from the operator. As the input unit 116, it is possible to use a pointing device such as a mouse or a trackball, a selection device such as a mode switch, or an input device such as a keyboard as appropriate.

The imaging control unit 117 includes a central processing unit (CPU), a memory, and the like, not illustrated, and performs overall imaging control of the MRI apparatus.

FIG. 2 is a block diagram illustrating the functional configurations of the coil unit 102 and the wireless unit 112. In FIG. 2, the same reference signs are applied to the same components as those of FIG. 1, and redundant explanations are omitted.

The coil unit 102 includes an RF receiver coil 201, an RF receiver unit 202, an ADC 203, a data communication unit 204, a data communication antenna 205, a clock transfer unit 206, a clock transfer antenna 207, and a control unit 208.

The RF receiver coil 201 receives MR signals emitted from the subject 118 to acquire electrical echo signals.

The RF receiver unit 202 amplifies the echo signals acquired by the RF receiver coil 201. Specifically, the RF receiver unit 202 is configured with a variable amplifier, not illustrated, which amplifies the echo signals to an appropriate level in the previous stage of the ADC 203 to suppress the effect of quantization errors. Note here that the RF receiver unit 202 is an example of a magnetic resonance signal detection unit.

The ADC 203 performs analog-to-digital conversion of the echo signals that are analog signals output by the RF receiver unit 202 based on the sampling clock supplied by the control unit 208 to acquire the echo data as the digital signals. Note here that the ADC 203 is an example of an analog-to-digital conversion unit.

The data communication unit 204 generates a communication frame by adding a header and the like to the echo data input from the ADC 203. Specifically, the data communication unit 204 is configured with a modulation/demodulation circuit, a frequency conversion circuit, a power amplification circuit, and the like, not illustrated. The data communication unit 204 performs modulation processing, frequency conversion processing, and the like on the communication frame to generate wireless communication signals, and transmits those from the data communication antenna 205. The data communication unit 204 also receives wireless communication signals transmitted from the data communication unit 222 via the data communication antenna 205. Then, frequency conversion processing, demodulation processing, and the like are performed on the received wireless communication signals to acquire reception data. Note that the data communication unit 204 may be configured to control wireless communication in compliance with the IEEE 802.11 standard. The data communication unit 204 may also be configured to control wireless communication in compliance with communication standards such as Bluetooth (registered trademark), NFC, UWB, Zigbee, and MBOA. UWB is an abbreviation for Ultra Wide Band, and MBOA is an abbreviation for Multi Band OFDM Alliance. Note here that OFDM is an abbreviation for Orthogonal Frequency Division Multiplexing. Furthermore, NFC is an abbreviation for Near Field Communication. Wireless USB, wireless 1394, Winet, and the like are included in UWB. Note here that the data communication unit 204 is an example of a second data communication unit.

The clock transfer unit 206 receives the wireless clock signal transmitted by a clock transfer unit 224 via the clock transfer antenna 207. Note here that the wireless clock signal is a wireless signal for synchronizing the system clocks of the main unit 101 and the coil unit 102. The clock transfer unit 206 generates a system clock from the wireless clock signal received by the clock transfer antenna 207, and outputs it to the control unit 208. Note here that the clock transfer unit 206 is an example of a clock receiver unit.

The control unit 208 controls operations of the coil unit 102 based on the system clock output by the clock transfer unit 206. The control unit 208 also generates a sampling clock from the system clock using a phase locked loop (PLL) circuit, not illustrated, and outputs it to the ADC 203.

The wireless unit 112 opposing to the coil unit 102 includes a control unit 221, a data communication unit 222, a data communication antenna 223, the clock transfer unit 224, and a clock transfer antenna 225.

The control unit 221 wirelessly transmits pulse sequence information input from the imaging control unit 117 to the coil unit 102 by the data communication unit 222. The control unit 221 also controls operations of the clock transfer unit 224 based on the pulse sequence information.

The configurations of the data communication unit 222 and the data communication antenna 223 are the same as those of the data communication unit 204 and the data communication antenna 205. The data communication unit 222 receives wireless communication signals transmitted from the data communication unit 204 via the data communication antenna 223. Then, The data communication unit 222 acquires echo data from the received wireless communication signals and outputs the echo data to the data analysis unit 113. Furthermore, the data communication unit 222 generates the wireless communication signals from the pulse sequence information input from the control unit 221, and transmits those to the coil unit 102. Note here that the data communication unit 222 is an example of a first data communication unit.

The clock transfer unit 224 generates wireless clock signals based on input from the clock generation unit 111 and the control unit 221, and transmits those from the clock transfer antenna 225. Note here that the clock transfer unit 224 is an example of a clock transmitter unit.

Subsequently, configurations and operations of the clock transfer unit 206 and the clock transfer unit 224 will be described.

Figure 3:
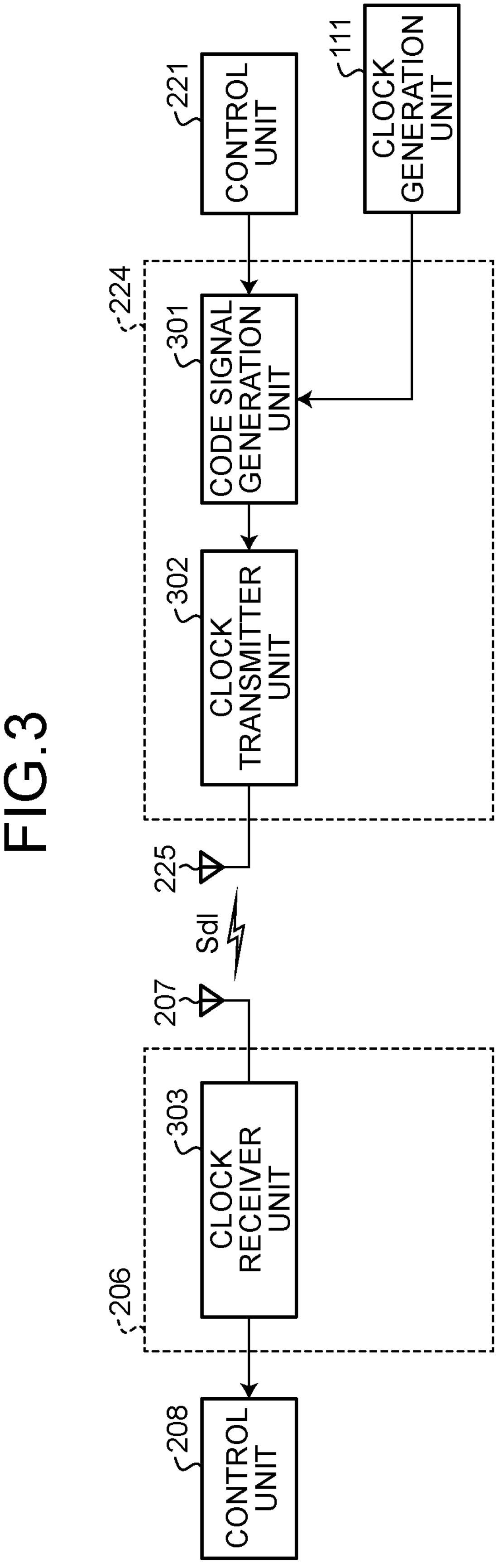
FIG. 3 is a block diagram illustrating functional configurations of clock transfer units.

FIG. 3 is a block diagram illustrating the functional configurations of the clock transfer units 206 and 224.

The clock transfer unit 224 transmits a wireless signal acquired by frequency-modulating a binary signal based on a first clock signal generated from a first system clock by the clock generation unit 111. Note here that the binary signal has a DC balance of substantially 0 at least in the transmission period of the wireless signal. Furthermore, the binary signal is a random signal with a run-length of 5 or less.

Specifically, the clock transfer unit 224 includes a code signal generation unit 301 and a clock transmitter unit 302.

The code signal generation unit 301 generates a code signal that is encoded based on the first clock signal input from the clock generation unit 111, and outputs it to the clock transmitter unit 302.

The clock transmitter unit 302 generates a wireless clock signal Sd1 based on the code signal input from the code signal generation unit 301, and transmits it from the clock transfer antenna 225.

The clock transfer unit 206 generates a second clock signal by dividing the wireless signal received from the clock transfer unit 224, and generates a second system clock from the generated second clock signal. Note here that frequencies of the second system clock and the first system clock are the same.

Specifically, the clock transfer unit 206 includes a clock receiver unit 303.

The clock receiver unit 303 receives the wireless clock signal Sd1 transmitted from the clock transfer unit 224 via the clock transfer antenna 207. Then, the clock receiver unit 303 generates a second clock signal from the wireless clock signal Sd1, and further generates a second system clock from the second clock signal and outputs it to the control unit 208. At this time, the second clock signal is equivalent to the first clock signal, and the system clocks of the entire MRI apparatus are synchronized. However, when frequency division or the like is performed by the control unit 208, the second clock signal and the first clock signal may be in a relationship of integer multiple or integer fraction.

Figure 4:
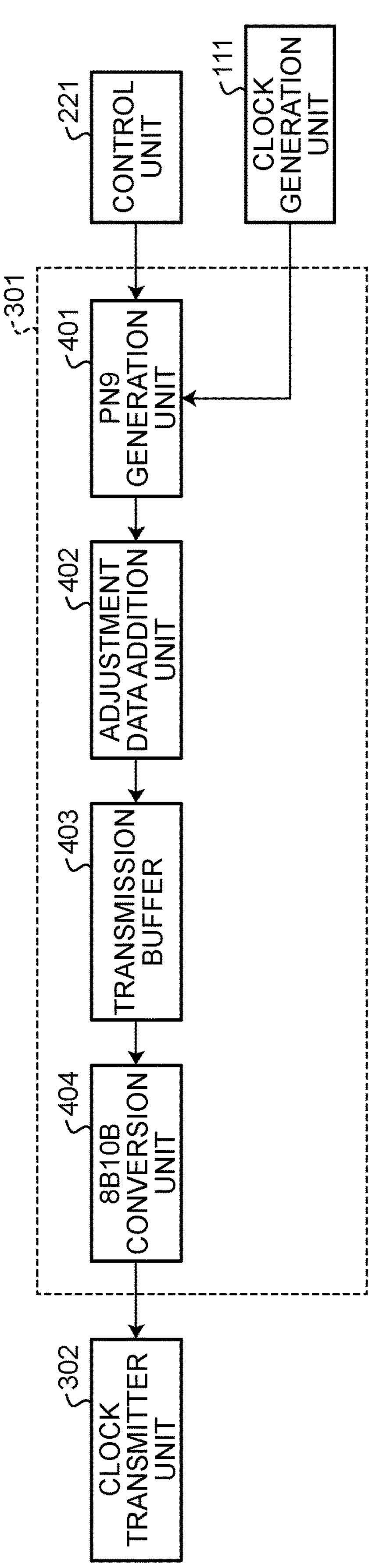
FIG. 4 is a block diagram illustrating a functional configuration of a code signal generation unit.

FIG. 4 is a block diagram illustrating the functional configuration of the code signal generation unit 301.

The code signal generation unit 301 includes a PN9 generation unit 401, an adjustment data addition unit 402, a transmission buffer 403, and an 8B10B conversion unit 404.

The PN9 generation unit 401 generates a PN9 code with a 511-bit signal cycle based on the first clock signal input from the clock generation unit 111, and outputs it to the adjustment data addition unit 402. The PN9 generation unit 401 also controls the generation timing of the PN9 code based on the pulse sequence information input from the control unit 221. For example, the PN9 generation unit 401 initializes the PN code after the power is turned on. For example, the PN9 generation unit 401 initializes the PN9 code triggered by a reset signal that indicates the timing when the power of the MRI apparatus is turned on or when measurement is started.

The adjustment data addition unit 402 adds bits to correct the direct current (DC) balance for each PN9 code period. Specifically, the adjustment data addition unit 402 adds one bit "0" or "1" to each 511-bit signal of the PN9 code input from the PN9 generation unit 401, and outputs a signal with a data length of 512 bits to the transmission buffer 403. At this time, since the PN9 code length is odd, either "0" or "1" is one bit less. However, the number of "0" and the number of "1" are matched by the correction bit.

The transmission buffer 403 stores therein the PN9 code with the correction bit generated by the adjustment data addition unit 402 as one frame of 8 bits.

The 8B10B conversion unit 404 converts an 8-bit input signal from the transmission buffer 403 into a 10-bit output signal and outputs it to the clock transmitter unit 302 according to a specified conversion table. At this time, in 8B10B encoding, the DC balance of the output data sequence is maintained by the control performed based on the running disparity (RD) value. That is, this control causes the number of "0" and the number of "1" appearing in the output data sequence to match or almost match. Furthermore, another characteristic of the 8B10B encoding is that five or more consecutive values of "0" and "1" do not appear.

Figure 5:
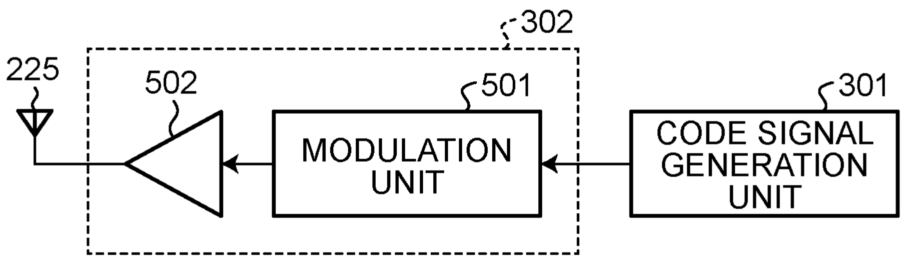
FIG. 5 is a block diagram illustrating a functional configuration of a clock transmitter unit.

FIG. 5 is a block diagram illustrating the functional configuration of the clock transmitter unit 302.

The clock transmitter unit 302 includes a modulation unit 501 and an amplification unit 502.

The modulation unit 501 frequency-modulates a frame of PN9 code using a binary continuous phase frequency shift keying (CPFSK) scheme. Specifically, the modulation unit 501 is configured with a mixer circuit, a band limiting filter, and PLL circuit, not illustrated, and converts the code signal input from the code signal generation unit 301 into a wireless frequency signal with a prescribed frequency. Here, assuming that the center frequency of the wireless signal is f1 [Hz] and the frequency shift by CPFSK modulation is ±f2 [Hz], the frequency of the wireless signal output from the modulation unit 501 is either f1−f2 [Hz] or f1+f2 [Hz]. Then, by an operation of the code signal generation unit 301, the disparity for each frame is adjusted to either 0 or ±2. Therefore, the time lengths of the f1−f2 [Hz] wireless signal period and the f1+f2 [Hz] wireless signal period are stably matched by performing observation over the medium to long term including a plurality of frames. Here, although not limited, a modulation index m for the CPFSK modulation is desirable to be 0.5.

The amplification unit 502 amplifies the signal input from the modulation unit 501, and transmits it as a wireless clock signal from the clock transfer antenna 225.

Figure 6:
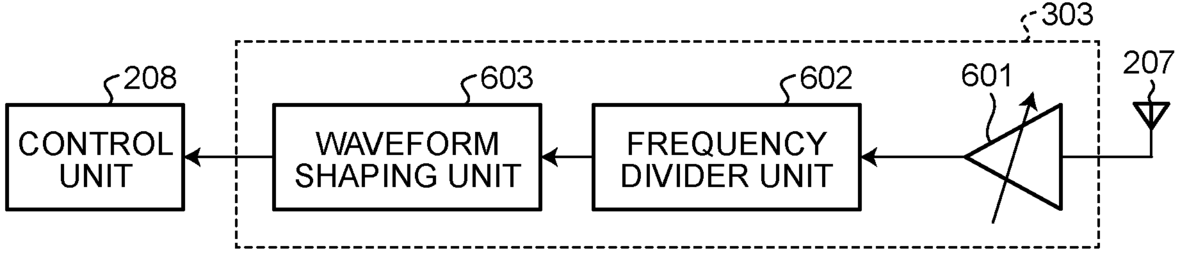
FIG. 6 is a block diagram illustrating a functional configuration of a clock receiver unit.

FIG. 6 is a block diagram illustrating the functional configuration of the clock receiver unit 303.

The clock receiver unit 303 includes a variable gain amplification unit 601, a frequency divider unit 602, and a waveform shaping unit 603.

The variable gain amplification unit 601 adjusts the level of the wireless clock signal received by the clock transfer antenna 207. Specifically, the variable gain amplification unit 601 is configured with an automatic gain control (AGC) circuit and a band limiting filter, not illustrated, and adjusts the signal input from the clock transfer antenna 207 to a signal of an appropriate level.

The frequency divider unit 602 generates a clock signal from the signal input from the variable gain amplification unit 601, and outputs it to the control unit 208 via the waveform shaping unit 603. Specifically, the frequency divider unit 602 is configured with a PLL circuit or a prescaler circuit, not illustrated, and the waveform shaping unit 603 is configured with a PLL circuit with a jitter cleaner function.

Figures 7A, 7B:
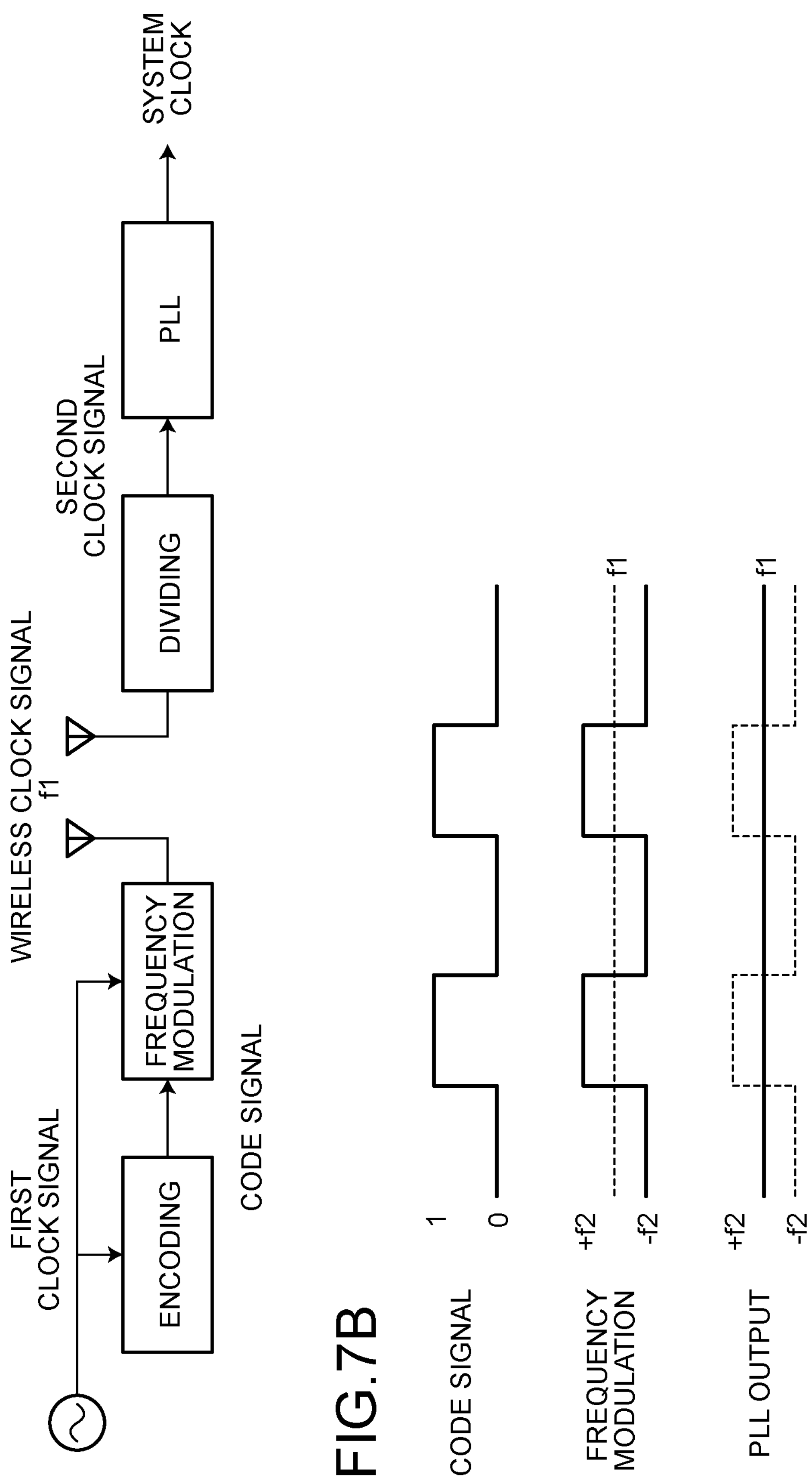
FIGS. 7A and 7B are diagrams illustrating clock control performed by the clock transfer units.

FIGS. 7A and 7B are diagrams illustrating clock control performed by the clock transfer units 206 and 224.

As illustrated in FIG. 7A, with the above configuration, the clock transfer unit 224 in the main unit 101 generates a code signal based on the first clock signal generated from the first system clock by the code signal generation unit 301 ("encoding" illustrated in FIG. 7A), and transmits a wireless clock signal acquired by frequency-modulating the code signal ("frequency modulation" illustrated in FIG. 7A) by the clock transmitter unit 302.

Here, code information generated by the code signal generation unit 301 is encoded such that the DC balance becomes substantially 0, that is, the number of "0" and the number of "1" included in the signal match or almost match, and "0" or "1" does not continue for a long period, as illustrated in the top row of FIG. 7B. Then, the wireless clock signal transmitted by the clock transmitter unit 302 is frequency-modulated such that the DC balance becomes substantially 0 and the frequency is either f1−f2 [Hz] or f1+f2 [Hz], as illustrated in the middle row of FIG. 7B.

The clock transfer unit 206 included in the coil unit 102 then divides the wireless clock signal received from the clock transfer unit 224 by the clock receiver unit 303 to generate a second clock signal ("dividing" illustrated in FIG. 7A), and generates a second system clock from the second clock signal and outputs it to the control unit 208 ("PLL" illustrated in FIG. 7A) by the PLL circuit included in the clock receiver unit 303.

Here, if the DC balance of the wireless clock signal transmitted by the clock transfer unit 224 of the main unit 101 is not 0, that is, if the number of "0" and the number of "1" in the wireless clock signal do not match, or if "0" or "1" continues for a long period, it accordingly causes frequency fluctuations in the second system clock output from the PLL circuit included in the clock receiver unit 303 of the coil unit 102.

In contrast, with the above configuration, the wireless clock signal transmitted by the clock transmitter unit 302 is frequency-modulated such that the DC balance becomes substantially 0 and the frequency is either f1−f2 [Hz] or f1+f2 [Hz]. Thus, as illustrated in the bottom row of FIG. 7B, the frequency of the second system clock output from the PLL circuit becomes substantially constant at f1 [Hz]. As a result, the frequency of the second system clock and the frequency of the first system clock become equal, which makes it possible to reduce the clock phase shift caused due to fading.

In addition, the above configuration does not have a unit for generating a modulated clock signal by demodulation, so that the power consumption can be suppressed low when driven by battery.

Subsequently, operations of the main unit 101 and the coil unit 102 in the MRI apparatus according to the present embodiment will be described.

Figure 8:
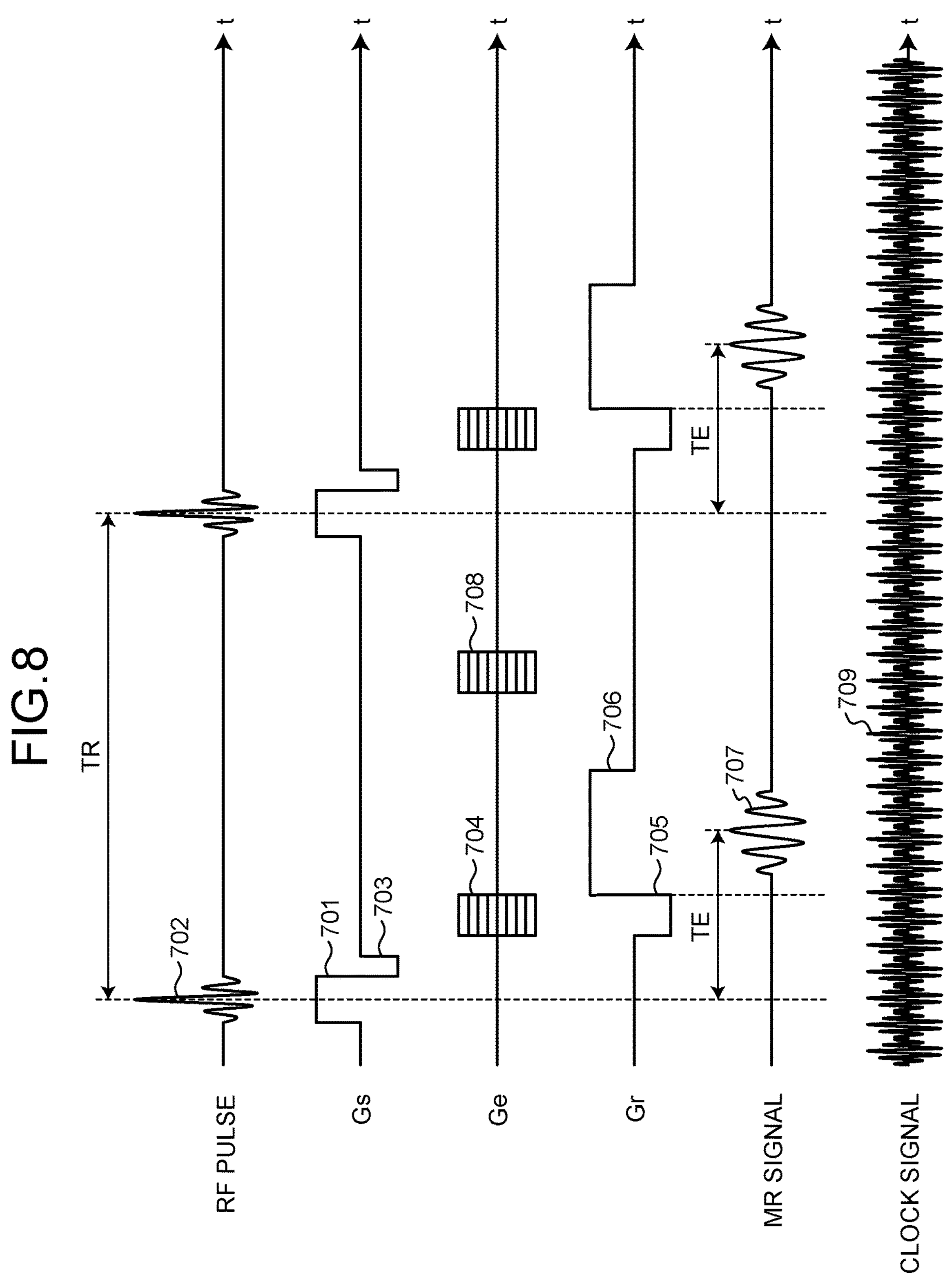
FIG. 8 is a timing chart illustrating a pulse sequence of the gradient echo method.

FIG. 8 is a timing chart illustrating a pulse sequence of the gradient echo method as an example of the operation of the present embodiment.

In FIG. 8, the top row indicates an RF pulse, the second from the top indicates the slice selection gradient magnetic field Gs, the third from the top indicates the phase encoding gradient magnetic field Ge, the fourth from the top indicates the readout gradient magnetic field Gr, the fifth from the top indicates an MR signal, and the sixth from the top indicates a wireless clock signal.

In the pulse sequence of the gradient echo method, an excitation RF pulse 702 with a flip angle of, for example, 90° is first transmitted to the imaging area simultaneously with the application of a slice selection gradient magnetic field pulse Gs 701 with a positive polarity, for example. Next, transmission of the excitation RF pulse 702 is stopped, and a slice selection gradient magnetic field pulse Gs 703 with reversed polarity is applied. The slice selection gradient magnetic field pulse Gs 703 is called a rephasing lobe, and its application period is approximately half the application period of the slice selection gradient magnetic field pulse Gs 701 before the polarity reversal. Next, a phase encoding gradient magnetic field Ge 704 and a readout gradient magnetic field Gr 705 whose polarity is, for example, negative are applied. Thereafter, a readout gradient magnetic field Gr 706 with reversed polarity is applied. Then, since an MR signal 707 is emitted from the subject 118 centered on the timing of echo time TE, the MR signal 707 is detected by the RF receiver coil 201 under the application of the readout gradient magnetic field Gr 706. Then, after completing the application of the readout gradient magnetic field Gr 706, a phase encoding gradient magnetic field Ge 708 whose polarity is reversed from that of the previously applied phase encoding gradient magnetic field Ge 704 is applied. Thereby, the effect of the phase encoding gradient magnetic field Ge 704 that is applied before detection of the MR signal 707 is eliminated before collecting the MR signal in the next phase encoding step. The operation heretofore is collection of the MR signal for one phase encoding step (one cycle), which is the processing within one repetition time TR in FIG. 8. This one cycle is repeated as many times as the number of phase encoding steps to collect the MR signals for one image.

In the pulse sequence described above, the clock transfer unit 224 continuously transmits a wireless clock signal 709. The coil unit 102 generates a system clock from the wireless clock signal 709, and performs analog-to-digital conversion of the MR signal 707 based on the sampling clock acquired from the system clock.

While the pulse sequence of the gradient echo method is described herein for simplifying the explanation, it is equally applicable to other pulse sequences of the spin echo method and the like.

Furthermore, while an example of the case using CPFSK signals as the wireless clock signals is described in the present embodiment, the technology disclosed in the present application is not limited thereto, and frequency modulation signals that are not phase continuous may also be used.

Moreover, with the present embodiment, it is also possible to superimpose a control signal on the wireless clock signal. In this case, the code signal generation unit 301 superimposes a control signal defining the operating state of the coil unit 102 on the wireless clock signal. Furthermore, the clock receiver unit 303 demodulates the received wireless clock signal and extracts the control signal.

For example, the clock receiver unit 303 demodulates the reset timing of the PN9 code from the received wireless clock signal to acquire the timing of the control signal. Alternatively, the clock receiver unit 303 extracts a K code that defines the control signal with the 8B10B code from the received wireless clock signal to acquire the timing of the control signal.

Figures 9, 10:
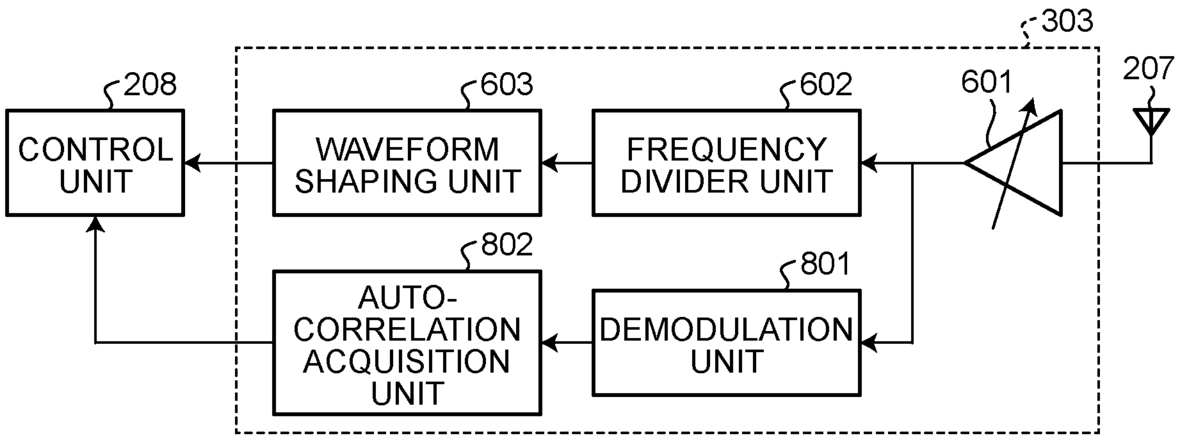
FIG. 9 is a block diagram illustrating a functional configuration of the clock receiver unit.
FIG. 10 is a diagram illustrating a configuration example of a control frame.

FIG. 9 is a block diagram illustrating a functional configuration of the clock receiver unit 303 for demodulating the reset timing of the PN9 code. In FIG. 9, the same reference signs are applied to the same components as those of FIG. 6, and redundant explanations are omitted.

The clock receiver unit 303 further includes a demodulation unit 801 and an autocorrelation acquisition unit 802.

The demodulation unit 801 generates a PN9 code by demodulation processing from the signal input from the variable gain amplification unit 601. Specifically, the demodulation unit 801 is configured with a mixer circuit, an ADC, a phase acquisition circuit, an unwrapping circuit, and a frequency acquisition circuit, not illustrated, and demodulates the PN9 code that is a clock signal component with a prescribed frequency from the signal input from the variable gain amplification unit 601.

The autocorrelation acquisition unit 802 calculates the autocorrelation of the PN9 code input from the demodulation unit 801, and acquires the timing of the control signal.

When the reset timing is demodulated, constant operation is not necessary. Thus, compared to the case with a unit for generating a modulated clock signal by demodulation, power consumption when driven by battery can be suppressed low.

FIG. 10 is a diagram illustrating a configuration example of a control frame generated by the code signal generation unit 301 for receiving the K code that defines the control signal with the 8B10B code.

The 8B10B conversion unit 404 sets the initial RD value to RD- and superimposes a control signal at the beginning of the control frame by a code indicating start of frame (SOF) when 8B10B-encoding the data input from the transmission buffer 403.

As the code for SOF, the K code defined by 8B10B encoding is used.

The control frame is configured with a SOF field 901, a payload field 902, and a correction bit field 903. As described above, the SOF field 901 is a field that indicates the start of the control frame, where the K code defined by the 8B10B encoding is placed. In the payload field 902, the data acquired by 8B10B-encoding the data input from the transmission buffer 403 is placed. In the correction bit field 903, "0" or "1" for correction, which is determined based on the result of the 8B10B conversion of the SOF field 901 and the payload field 902, is placed. Here, the control frame lengths are, for example, 10 bits for the SOF field 901, 501 bits for the payload field 902, and 1 bit for the correction bit field 903, totaling 512 bits.

Furthermore, in the present embodiment, wireless signals are transmitted and received over two links between the data communication unit 204 and the data communication unit 222 and between the clock transfer unit 206 and the clock transfer unit 224. The wireless signals of each link are desirable to be isolated so as not to affect each other. For example, it is possible to use the frequency division multiplexing (FDM) scheme that ensures isolation by using a different carrier frequency for each link. It is also possible to use the space division multiplexing (SDM) scheme that ensures isolation by antenna directivity of each link. When isolating each of the links using the FDM scheme, the antennas of each of the links may be shared by using a filter element such as a diplexer.

Furthermore, while the operation principle of the 8B10B encoding performed while adding correction bits to the PN9 code as the encoding method for wireless clock signals is described in the present embodiment, all combinations of the above are included in the technology disclosed in the present application.

It is also possible to use other encoding methods such as 64B66B and 128B130B, which are capable of acquiring the same effect as that of 8B10B that balances the DC balance according to the input data.

Furthermore, the technology disclosed in the present application is also implemented by executing the following processing. That is, it is the processing executed by supplying software (computer program) that implements the functions of the embodiment described above to a system or an apparatus via a network or various kinds of storage media, and reading out the computer program by a computer (or CPU, micro processing unit (MPU), or the like) of the system or the apparatus. It may also be executed by a circuit (for example, application specific integrated circuit (ASIC)) that implements one or more functions.

According to the embodiment described above, it is possible to improve accuracy of reconstructed images by reducing the clock phase shift caused due to fading while suppressing the power consumption of the coil unit 102.

In the embodiment described above, for example, each of the processing units included in the main unit 101 and the coil unit 102 may also be implemented by a single piece of or a plurality of pieces of processing circuitry. In this case, the processing circuitry is implemented by, for example, a processor. In this case, the processing functions of the processing circuitry are stored in a storage in the form of a computer program that can be executed by a computer, for example. Then, the processing circuitry reads out and executes the computer programs from the storage to implement the processing functions corresponding to the computer programs.

Note here that the processing circuitry, for example, may be configured with a combination of a plurality of independent processors to implement each of the processing functions by executing the computer programs with each of the processors. Furthermore, the processing functions of the processing circuitry may be distributed or integrated into a single piece of or a plurality of pieces of processing circuitry as appropriate. The storage in which the computer programs corresponding to the processing functions are stored may be a single storage. Alternatively, a plurality of storages may be arranged in a distributed manner for each piece of the processing circuitry, and each piece of the processing circuitry may read out the corresponding computer program from the individual storage.

Furthermore, each of the processing units included in the main unit 101 and the coil unit 102 may be implemented by hardware alone, software alone, or a combination of hardware and software, in addition to being implemented by the processing circuitry.

While an example in which a "processor" reads out and executes a computer program corresponding to each of the processing functions from a storage is described above, the embodiment is not limited thereto. The term "processor" means, for example, a circuit such as a central processing unit (CPU), a graphics processing unit (GPU), an application specific integrated circuit (ASIC), and a programmable logic device (for example, a simple programmable logic device (SPLD), a complex programmable logic device (CPLD), and a field programmable gate array (FPGA)). When the processor is a CPU, for example, the processor reads out and executes the computer program stored in the storage to implement each of the processing functions. On the other hand, when the processor is an ASIC, the processing function is directly installed in the circuit of the processor as the logic circuit, instead of saving the computer program in the storage. Note that each of the processors of the present embodiment is not limited to being configured as a single circuit for each processor, and may also be configured as a single processor by combining a plurality of independent circuits to implement the processing functions. Furthermore, it is also possible to integrate a plurality of structural components in FIG. 1 into a single processor to implement the processing functions.

Note here that the computer program to be executed by the processor is provided by being installed in advance in a read-only memory (ROM), a storage, or the like. The computer program may be provided in a file of format that can be installed on such devices or in an executable format by being recorded on a computer readable non-transitory storage medium such as a compact disc (CD)-ROM, a flexible disk (FD), a CD-recordable (R), a digital versatile disc (DVD), or the like. Furthermore, the computer program may also be stored on a computer connected to a network such as the Internet, and provided or distributed by being downloaded via the network. For example, the computer program is configured with modules including each of the functional units described above. As for the actual hardware, the CPU reads out and executes the computer program from a storage medium such as a ROM, so that each of the modules is loaded onto a main memory device and generated on the main memory device.

Furthermore, in the embodiment described above, each of the structural components of each of the illustrated apparatuses is the functional concept and is not necessarily need to be physically configured as illustrated in the drawings. In other words, the specific forms of distribution and integration of the apparatuses are not limited to those illustrated in the drawings, but all or some of them can be functionally or physically distributed or integrated in any unit in accordance with various kinds of load, use state, or the like. Furthermore, all or some of the processing functions performed by respective apparatuses can be implemented by the CPU and the computer program that is analyzed and executed by the CPU, or may be implemented by hardware using wired logic.

Regarding the processing described in the above embodiment, all or several pieces of the processing described to be performed automatically can be performed manually, or all or several pieces of the processing described to be performed manually can be performed automatically using a known method. In addition to the above, the processing procedures, control procedures, specific names, and information including various kinds of data and parameters discussed in the description and drawings can be changed as appropriate, unless otherwise noted.

According to at least one of the embodiments described above, it is possible to improve accuracy of reconstructed images by reducing the clock phase shift caused due to fading while suppressing the power consumption of the coil apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus, comprising:
a main apparatus; and
a coil apparatus that is separate from the main apparatus, wherein
the main apparatus generates a binary signal based on a first clock signal that is generated from a first clock of the main apparatus, frequency-modulates the generated binary signal so as to convert the binary signal into a wireless signal with a predetermined frequency, and transmits the wireless signal,
the coil apparatus generates a second clock signal by dividing the received wireless signal, and generates a second clock of the coil apparatus from the generated second clock signal, and
frequencies of the second clock and the first clock are identical.

2. A magnetic resonance imaging apparatus, comprising:
a main apparatus; and
a coil apparatus that is separate from the main apparatus, wherein
the main apparatus comprises processing circuitry configured to:
generate a first clock signal from a first clock of the main apparatus;
generate a binary signal based on a first clock signal that is generated from a first clock of the main apparatus, frequency-modulates the generated binary signal so as to convert the binary signal into a first electrical signal with a predetermined frequency, and transmit the first electrical signal to the coil apparatus by first wireless communication; and
receive a second electrical signal transmitted from the coil apparatus, the coil apparatus comprises processing circuitry configured to:

generate a second clock signal by dividing the first electrical signal transmitted from the main apparatus, and generate a second clock of the coil apparatus from the generated second clock signal;

output, as the second electrical signal, a magnetic resonance signal emitted as an electromagnetic wave from a subject;

digitalize the second electrical signal based on the second clock; and transmit the digitalized second electrical signal to the main apparatus by second wireless communication, and frequencies of the first clock and the second system clock are identical.

3. The magnetic resonance imaging apparatus according to claim 1, wherein the binary signal has a DC balance of substantially 0 at least in a transmission period of the wireless signal.

4. The magnetic resonance imaging apparatus according to claim 1, wherein the binary signal is a random signal with a run length of 5 bits or less.

5. The magnetic resonance imaging apparatus according to claim 1, wherein the main apparatus initializes the binary signal after power is turned on.

6. The magnetic resonance imaging apparatus according to claim 1, wherein the main apparatus superimposes a control signal defining an operating state of the coil apparatus on the wireless signal.

7. The magnetic resonance imaging apparatus according to claim 1, wherein the main apparatus comprises processing circuitry configured to:

generate the first clock signal from the first clock;

frequency-modulate the binary signal so as to convert the binary signal into a first electrical signal with a predetermined frequency, and transmit the first electrical signal as the wireless signal to the coil apparatus by wireless communication; and receive a second electrical signal from the coil apparatus, the second electrical signal being acquired by digitalizing a magnetic resonance signal emitted as an electromagnetic wave from a subject based on the second clock.

8. The magnetic resonance imaging apparatus according to claim 1, wherein the coil apparatus comprises processing circuitry configured to:

generate the second clock signal by dividing the wireless signal, and generate the second clock from the second clock signal;

output, as a second electrical signal, a magnetic resonance signal emitted as an electromagnetic wave from a subject;

digitalize the second electrical signal based on the second clock; and transmit the digitalized second electrical signal to the main apparatus by wireless communication.

9. The magnetic resonance imaging apparatus according to claim 2, wherein frequencies of the first wireless communication and the second wireless communication are different.

10. The magnetic resonance imaging apparatus according to claim 3, wherein the main apparatus adds a bit for correcting the DC balance for each cycle of the binary signal.

11. The magnetic resonance imaging apparatus according to claim 6, wherein the coil apparatus demodulates the wireless signal, and extracts the control signal.

* * * * *